United States Patent [19]

Tominaga et al.

[11] 4,289,032

[45] Sep. 15, 1981

[54] METHOD OF DISCRIMINATING KINDS OF GOLF BALLS

[75] Inventors: Ichiro Tominaga; Teruo Sasaki, both of Kobe, Japan

[73] Assignee: Sumitomo Rubber Industries, Inc., Kobe, Japan

[21] Appl. No.: 89,736

[22] Filed: Oct. 31, 1979

[30] Foreign Application Priority Data

Nov. 8, 1978 [JP] Japan ................................. 53-137638

[51] Int. Cl.³ ............................................ G01N 29/00
[52] U.S. Cl. ..................................... 73/599; 273/213
[58] Field of Search ................ 73/599, 600, 597, 598, 73/579; 273/213, 216, 218, 222

[56] References Cited

U.S. PATENT DOCUMENTS

| | | | |
|---|---|---|---|
| 2,175,685 | 10/1939 | Dieterich | 273/216 |
| 2,667,063 | 1/1954 | Cunningham, Jr. | 73/598 |
| 4,147,064 | 4/1979 | Bond | 73/597 |

OTHER PUBLICATIONS

H. J. McSkimin et al., "Water Immersion Tech. Measuring Attenuation and Phase Velocity of Longitudinal Waves in Plastics", *J. Acous. Soc. Am.*, vol. 49, No. 3, (Part 2), pp. 713-722, Mar. 1971.

*Primary Examiner*—Stephen A. Kreitman
*Attorney, Agent, or Firm*—Birch, Stewart, Kolasch & Birch

[57] ABSTRACT

A method of discriminating solid golf balls from thread-wound golf balls which includes the steps of holding the golf ball to be discriminated between a transmitter coupled to an ultrasonic wave oscillator and a receiver coupled to an ultrasonic detector for detecting the ultrasonic wave received by the receiver, applying from the transmitter, the ultrasonic wave having a frequency which can propagate through the solid golf ball, but can not propagate therethrough, to the golf ball to be discriminated, and detecting presence of the ultrasonic wave reaching the receiver through the golf ball to be discriminated by the ultrasonic wave detector.

5 Claims, 5 Drawing Figures

METHOD OF DISCRIMINATING KINDS OF GOLF BALLS

BACKGROUND OF THE INVENTION

The present invention generally relates to non-destructive inspection and more particularly, to a method of discriminating kinds of golf balls through utilization of ultrasonic waves.

Commonly, the constructions of golf balls may be broadly divided into two types, i.e., one being the so-called thread-wound golf ball comprising a core portion of round shape, a flexible thread, for example, of rubber tightly wound around said core portion under the application of a tension to a certain extent, and an outer layer, for example, of gutta percha, plastics and the like applied onto said wound flexible thread for covering, and the other being the so-called solid golf ball which is made through one-piece molding, by subjecting to vulcanization during heating under pressure, a mixture including rubber, crosslinking resin, polymerization initiator and filling agent, etc. and filled in a mold. The present invention relates to a method of discriminating or distinguishing between the thread-wound golf balls and solid golf balls as described above.

Conventionally, the solid golf balls have been considered to be suitable only for exercise, but owing to various technical improvements, they have recently undergone a complete change so as to be usable also for actual play. At the present stage, however, the solid golf balls as described above are still inferior to the thread-wound golf balls in any of the important characteristics of golf balls such as shot feeling, resilience, trajectory, etc. Nevertheless, due to the fact that the former are similar in appearance to the latter, there is a possibility of undesirable mixing between the solid golf balls and thread-wound golf balls.

For preventing the mixture as described above, there has been strongly demanded a method of discriminating these golf balls as described above through non-destructive examination. In connection with the above, since golf balls are normally painted white, the appearance thereof is also an important factor as article, and therefore, any method which might give rise to soiling or small flaws, etc. on the surfaces of golf balls in the process of discriminating inspection is not preferable to be adopted.

SUMMARY OF THE INVENTION

Accordingly, an essential object of the present invention is to provide a method of discrimination between solid golf balls and thread-wound golf balls in an efficient manner through utilization of ultrasonic waves.

Another important object of the present invention is to provide a method of discrimination as described above which is simple in processing, and capable of distinguishing the solid golf balls from thread-wound golf balls without spoiling the appearance of the golf balls or any damages thereto.

In accomplishing these and other objects according to one preferred embodiment of the present invention, there is disclosed a method of discriminating solid golf balls from thread-wound golf balls which includes the steps of holding the golf ball to be discriminated between a transmitter coupled to means for oscillating ultrasonic wave and a receiver coupled to means for detecting the ultrasonic wave received by the receiver, applying from the transmitter, the ultrasonic wave having a frequency which can propagate through the solid golf ball, but can not propagate therethrough to the golf ball to be discriminated and detecting presence of the ultrasonic wave reaching the receiver through the golf ball to be discriminated by the ultrasonic wave detecting means.

By the simple arrangement according to the method of the present invention as described above, definite discrimination between the solid golf balls and thread-wound golf balls can be achieved in an efficient manner at an accuracy of 100%, without any soiling or injury of the golf balls to be discriminated.

BRIEF DESCRIPTION OF THE DRAWINGS

These and other objects and features of the present invention will become apparent from the following description taken in conjunction with the preferred embodiment thereof with reference to the accompanying drawings, in which.

Before the description of the present invention proceeds, it is to be noted that like items are designated by like reference symbols throughout several diagrams of the accompanying drawings.

DETAILED DESCRIPTION OF THE INVENTION

In the first place, it is to be noted that ultrasonic waves have almost no directivity in the comparatively low frequency range, and are uniformly radiated in all directions. In the vicinity of 20 KHz, the ultrasonic waves tend to have directivity to a certain extent, but in the case of high frequency higher than several hundred KHz, they are mostly radiated only in the forward direction, and in the ultra high frequency higher than several hundred KHz, especially above 1 MHz, are regarded to go straight in the similar manner as in light, without going around to the reverse side of an obstacle.

Meanwhile, although the thread-wound golf ball including the inner core portion around which the flexible thread, for example, of rubber is closely wound as described earlier is considered to have no gaps macroscopically, it actually has a layer of air so thin as will not be noticeable with naked eyes, and present between the turns of the flexible thread or between the flexible thread and the core portion, and in terms of model, it may be regarded that the rubber layers and air layers are piled up one upon another to provide, as it were, numerous air vents in the thread-wound ball.

Upon application of the ultrasonic waves of several hundred KHz, especially those above 1 MHz to such a structure as in the thread-wound golf ball as described above, the flexible thread becomes an obstacle when the sound waves passing through the flexible thread enters the air layer for subsequently advancing towards the flexible thread layers, with consequent attenuation of the sound waves to a large extent, and thus, the propagation of the sound waves is remarkably obstructed. If the state as described above is repeated, it becomes impossible for the sound waves to propagate through the thread-wound golf ball.

On the other hand, in the case of a low frequency of the order of 20 KHz or thereabout, the sound waves can be propagated through diffraction in the case of the thread-wound golf ball owing to the long wavelength.

Figure 1:
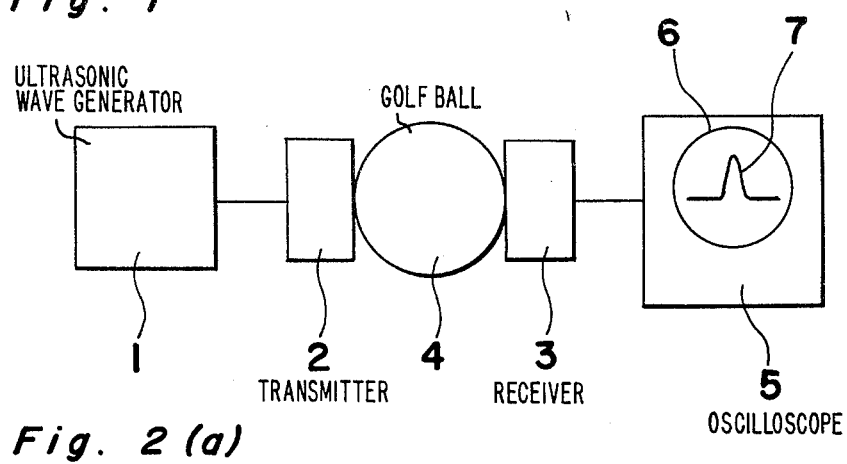
FIG. 1 is a schematic side elevational view of an ultrasonic flaw detector which may be employed for the discriminating method according to the present invention.

Referring now to the drawings, there is shown in FIG. 1 an arrangement for discriminating golf balls which includes an ultrasonic wave generator 1 coupled to a transmitter 2, a receiver 3 confronting the transmitter 2 in a spaced relation thereto, and coupled to an oscilloscope 5 or the like provided with a cathode ray tube 6. For the discrimination, the ultrasonic waves generated by the generator 1 is applied to a golf ball 4 to be tested which is held between the transmitter 2 and receiver 3, and the waveform 7 of the sound signal reaching the receiver 3 through the golf ball 4 is displayed on the cathode ray tube 6.

Accordingly, if the frequency is higher than several hundred KHz, especially above 1 MHz, the sound signal is detected on the cathode ray tube 6 of the oscilloscope 5 through propagation of the sound wave in the case of a solid golf ball, but in the case of a thread-wound golf ball, such signal is not observed on the cathode ray tube 6, since the sound wave is not propagated through such a thread-wound golf ball as described earlier.

Hereinbelow, examples are given to illustrate the effect of the present invention, without any intention of limiting the scope thereof.

EXAMPLE 1

For the ultrasonic wave generator, an ultrasonic flaw detector (model FD 210) manufactured by Mitsubishi Electric Corporation, Japan was employed, with two ceramic probes PC-1Z25N-M (1 MHz) being connected thereto for utilizing one of the probes as the transmitter and the other of the probes as the receiver, while an oscilloscope was employed for detection of the signal.

Figure 2:
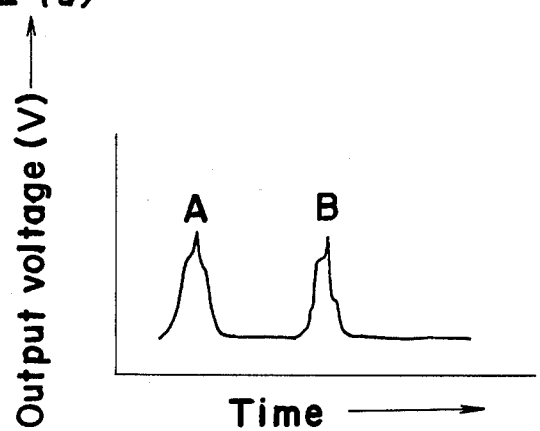
FIGS. 2(a) and 2(b) are diagrams representing waveforms to be observed on a cathode ray tube of an oscilloscope in comparison with oscillating waveforms when ultrasonic wave of 1 MHz is employed respectively for solid golf balls and thread-wound golf balls according to the discriminating method of the present invention.
Figure 2:
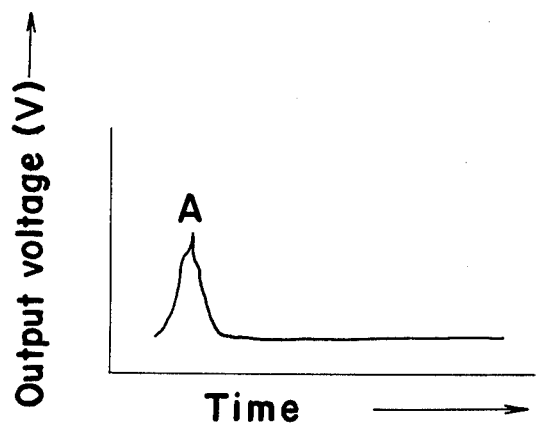

With the arrangement as described above, 1000 pieces of solid golf balls and another 1000 pieces of thread-wound golf balls were subjected to discriminating tests through detection of presence of signals, as a result of which discrimination at 100% probability could be achieved. More specifically, as shown in the diagram of FIG. 2(a) illustrating the waveform on the cathode ray tube when the ultrasonic wave of 1 MHz is employed in comparison with the oscillation waveform A, the propagation wave B was observed in the case of the solid golf ball due to propagation of the ultrasonic waves therethrough, and the solid golf balls could be clearly distinguished from the thread-wound balls for which no propagation wave was noticed as shown in FIG. 2(b).

EXAMPLE 2

Figure 3:
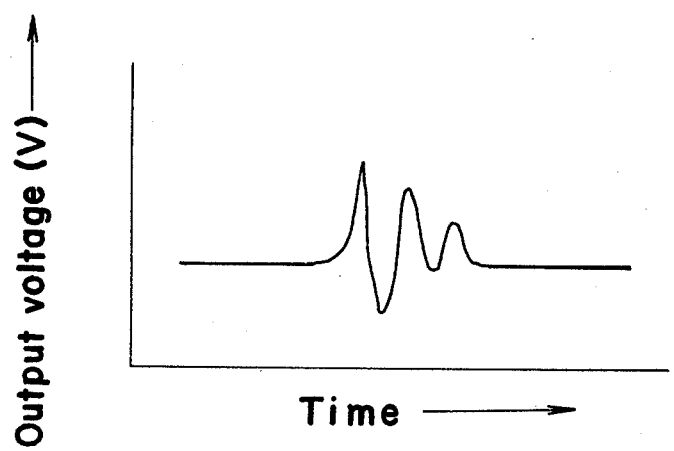
FIGS. 3(a) and 3(b) are diagrams similar to FIGS. 2(a) and 2(b) when ultrasonic wave of 20 KHz is employed according to the discriminating method of the present invention.
Figure 3:
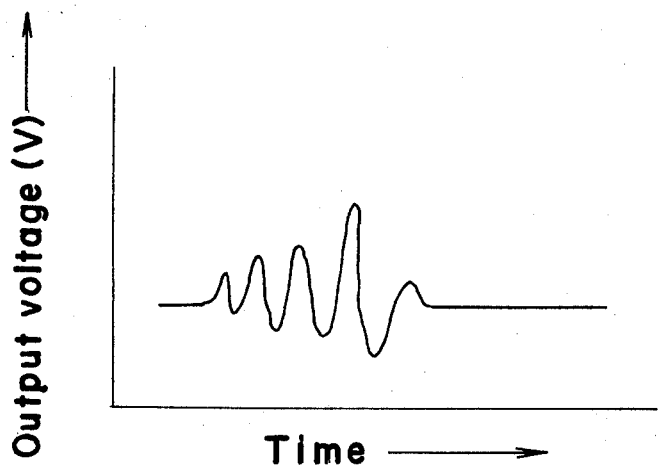

For the experiment, an ultrasonic wave tester made by Hokusei Denshi Co., Ltd., Japan was employed, with an ultrasonic wave oscillator of 20 KHz ferrite vibrator being used for the transmitter, while a ceramic probe was adopted for the receiver. In the frequency as described above, however, it was impossible to achieve a definite discrimination, since the ultrasonic waves were propagated through both of the solid golf balls and thread-wound golf balls to display signals on the cathode ray tube, without any distinctive difference therebetween as shown in FIG. 3(a) for the solid golf balls and FIG. 3(b) for the thread-wound golf balls.

As is clear from the foregoing description, according to the present invention, solid golf balls can be positively and readily differentiated from thread-wound golf balls in an efficient manner. Furthermore, since the golf balls to be distinguished are not subjected, for example, to strong external forces for discrimination through strain or stress as in the conventional methods, they are free from soiling, flaws, etc. without any reduction of commercial value.

It is to be noted here that, although flaw detection of metallic material, etc. has conventionally been effected by the non-destructive examination through utilization of the ultrasonic waves, there has been only a few instances where such non-destructive examination is successfully applied to rubber, plastic materials, and the like, probably because the waveforms obtained through propagation of the sound waves are not so clearly identified as in the case of metallic materials, and thus, the present invention is particularly characterized in providing the novel method of discriminating golf balls at an accuracy of 100% through application of the ultrasonic wave detection to the golf balls composed of rubber and plastic materials.

More specifically, the particular features of the present invention are such that, by selecting the ultrasonic waves having frequency that can be propagated through one object, but can not be propagated through the other object (this is possible due to the structural differences between the solid golf balls and thread-wound golf balls), the discrimination therebetween can be achieved at an accuracy of 100% in an efficient manner without necessity for identification of differences of complicated waveforms.

Needless to say, the application of the ultrasonic waves to the discrimination between the solid golf balls and thread-wound golf balls has not been known up to the present.

It should be also noted here that, in the foregoing embodiments, although the present invention is mainly described with reference to the discrimination between the solid golf balls and thread-wound golf balls, the method according to the present invention is not limited in its application to the distinguishment of golf balls alone, but may readily be applicable to discrimination between one object through which the ultrasonic wave of the predetermined frequency can propagate and the other object through which such ultrasonic wave can not propagate, and that the ultrasonic wave testers to be employed are not limited to those described as employed in the foregoing embodiments, but any other ultrasonic flaw detectors and the like may be employed so far as they meet the purpose of the present invention.

Although the present invention has been fully described by way of examples with reference to the accompanying drawings, it is to be noted that various changes and modifications are apparent to those skilled in the art. Therefore, unless otherwise such changes and modifications depart from the scope of the present invention, they should be construed as included therein.

What is claimed is:

1. A method of discriminating solid golf balls from thread-wound golf balls which comprises the steps of holding the golf ball to be discriminated between a transmitter coupled to means for oscillating ultrasonic wave and a receiver coupled to means for detecting the ultrasonic wave received by said receiver, applying from said transmitter, the ultrasonic wave having a frequency which can propagate through said solid golf ball, but can not propagate through said thread-wound golf ball, to said golf ball to be discriminated, and detecting presence of the ultrasonic wave reaching said receiver through said golf ball to be discriminated by said ultrasonic wave detecting means.

2. A method as claimed in claim 1, wherein said frequency of the ultrasonic wave to be applied to said golf ball to be discriminated is higher than several hundred KHz.

3. A method as claimed in claim 2, wherein said frequency of the ultrasonic wave to be applied to said golf ball to be discriminated is higher than 500 KHz.

4. A method as claimed in claim 2, wherein said frequency of the ultrasonic wave to be applied to said golf ball to be discriminated is higher than 1 MHz.

5. A method as claimed in claim 1, wherein said ultrasonic wave detecting means is an oscilloscope.

* * * * *